United States Patent [19]

Mezi

[11] Patent Number: 4,573,973
[45] Date of Patent: Mar. 4, 1986

[54] CASE FOR PROTECTING A SYRINGE BODY

[75] Inventor: Michel A. Mezi, Quetigny, France

[73] Assignee: Laboratoire Spad, Quetigny, France

[21] Appl. No.: 641,487

[22] Filed: Aug. 16, 1984

[30] Foreign Application Priority Data

Sep. 2, 1983 [FR] France ................. 83 14563

[51] Int. Cl.⁴ .............................................. A61M 5/00
[52] U.S. Cl. ................................... 604/197; 604/263; 206/571
[58] Field of Search ....................... 604/197, 198, 263; 206/571

[56] References Cited

U.S. PATENT DOCUMENTS

| 2,254,449 | 9/1941 | Rasmussen | 604/197 |
| 3,107,785 | 10/1963 | Roehr | 604/197 |
| 3,677,247 | 7/1972 | Brown | 604/197 |
| 3,890,971 | 6/1975 | Leeson et al. | 604/198 |
| 4,425,120 | 1/1984 | Sampson et al. | 604/198 |

Primary Examiner—John D. Yasko

[57] ABSTRACT

The case is constituted by a hollow tubular member which fits tightly on the outer face of the body. One end of this member is closed off by a solid wall. The length of the case is such that when the body is introduced into the latter, the tip for fixing the syringe on a gripping tool remains exposed. The needle which project outside the body is protected in an air tight manner inside the case, without contact with the inner faces of the latter. The case is provided internally with an abutment which limits the penetration of the syringe body into the case so that the needle does not reach the closing wall. Parts in relief of identical thickness distributed on the outer periphery of the case and on the open end of the cap ensure the locking of the cap on the case in an air-tight manner.

5 Claims, 4 Drawing Figures

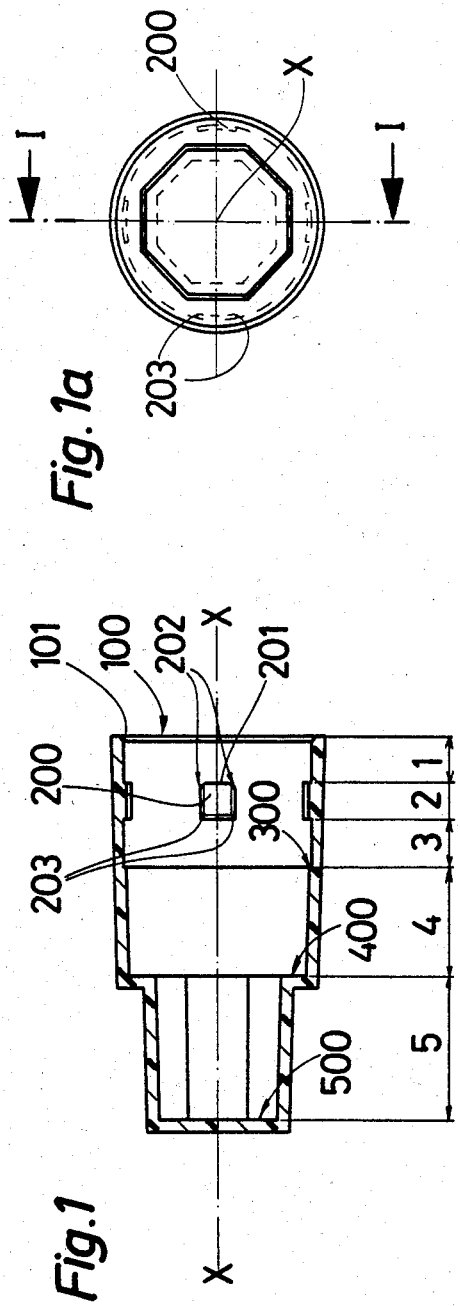
Fig.1a
Fig.1
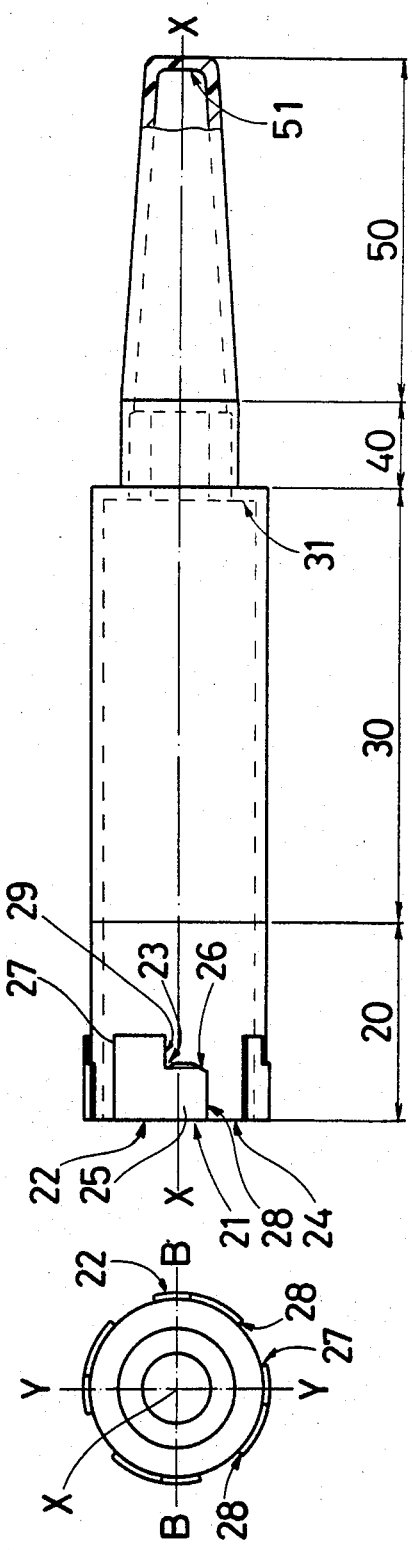
Fig.2
Fig.2a 4,573,973

CASE FOR PROTECTING A SYRINGE BODY

FIELD OF INVENTION

The invention relates to keeping disposable syringes sterile.

It relates to a case for protecting a syringe body.

The case is constituted by a hollow tubular member which fits tightly on the outer face of the body, one end of this member being closed off by a solid wall, the length of the case being such that when the body is introduced into the latter, the tip for fixing the syringe on a gripping tool remains exposed and the needle which projects outside the body is protected in an airtight manner inside the case, without contact with the inner faces of the latter, the case being provided internally with an abutment which limits the penetration of the syringe body into the case so that the needle does not reach the closing wall.

PRIOR ART

The French document No. 71 44606 describes improvements applied to syringes for injections, mainly composed of disposable parts, supplied in a sterile state, by means of a support for sterilization and presentation of the syringe body, cases and cartridges.

This support is characterized in that it comprises a base on which it rests and a wall rising from the base limiting a small cavity able to receive, with friction and in an air-tight manner, an end part of one of the members, case, cartridge, this end part, on a case containing a syringe body equipped with a cartridge, being its free end part which is open and through which the screwed-thread of the syringe body projects and, on a cartridge alone, this end part being the end part opposite that which is closed off by a piston.

The support thus described comprises a plurality of small cavities limited by walls rising from this base.

SUMMARY OF THE INVENTION

The object of the invention consists of producing a cap making each case independent of the others both for sterilization as well as for presentation.

To this end, the open end of the case is covered by a removable blind cap, having an inner diameter corresponding to the outer diameter of the said end of the case, so that this cap constitutes a virtually air-tight closure enclosing and protecting the syringe body in the case.

The open end of the case for protecting a syringe body comprises, equally distributed on the outer periphery of the case along equidistant generatrices parallel to the axis of symmetry of the case, parts in relief of identical thickness, in the form of angle members whereof one side, namely that which is directed towards the opening of the case, is situated on a single circumference, parallel to the rim of the said opening, the apex of each right angle being located on another single circumference which is parallel to the former.

The cap comprises, also distributed on its inner periphery in contact with the case along equidistant generatrices, parallel to its axis of symmetry, parts in relief of identical thickness, in the form of rectangles whereof the same side, directed towards the blind face of the cap, is situated on a single circumference parallel to the rim of the opening of the cap.

The peripheral spacing between the rectangles of the cap corresponds to the peripheral spacing between the sides of the angle members parallel to the axis of symmetry common in the case and to the cap, in order that fitting of the cap on the case introduces the rectangles between the angle members and that a rotation of the cap with respect to the case places these rectangles in the right angles of the angle members, all orientated in the same direction, in order to ensure locking of the cap on the case.

The cap comprises internally a circular shoulder parallel to the rim of its opening. This shoulder is placed at a distance from the said rim such that locking of the cap on the case presses said shoulder in an airtight manner against the peripheral rim of the opening of the case in order to make the arrangement of the case and cap virtually air-tight.

BRIEF DESCRIPTION OF THE DRAWINGS

Other advantages will become apparent from the description given as a non-limiting example, of one embodiment of the invention and of the drawings in which:

FIG. 1 is a longitudinal sectional view of the cap;

FIG. 1a is a cross-sectional view of FIG. 1;

FIG. 2 is a longitudinal sectional view of the case;

FIG. 2a is a cross-sectional view of FIG. 2

DESCRIPTION OF THE PREFERRED EMBODIMENTS

FIG. 1 makes it possible to define at least five adjacent areas of the blind cap covering the case:

the cylindrical area 1 comprises the opening 100 covering the corresponding opening of the case, provided with a chamfer 101 directed towards the inside of the cap in order to facilitate positioning of the cap on the case;

the cylindrical area 2 supporting the means for fixing and locking the cap on the case;

the cylindrical area 3 defined adjacent the opening 100 by the aforesaid fixing means and adjacent to the blind end by a circular shoulder 300 produced essentially by a difference in the bore between the areas 1,2 and the area 3 on the one hand, between the area 3 and the area 4 on the other hand;

the cylindrical or slightly conical area 4 is defined by the shoulder 300 adjacent the opening 100, by a step 400 adjacent the blind end;

the polygonal area 5, defined by the step 400 adjacent the opening and at the opposite end by the wall 500 which closes the cap and makes it blind. The polygonal shape of this area 5 facilitates gripping of the cap and its rotation at the time of locking or unlocking operations.

The fixing means of the area 2 are constituted by parts in relief in the shape of rectangles 200 whereof the side 201 directed towards the opening 100 is perpendicular to the axis of symmetry XX common to the cap and to the case.

These rectangles 200 of which there are four in the embodiment described, are of identical thickness and have identical dimensions. The sides 201 are arranged on a single circumference parallel to the opening 100. A slight chamfer 202 reduces the angles of the rectangles directed towards the opening 100.

The rectangles 200 are equidistant in the inner periphery of the area 2 of the cap, their angles 203 occupying a position forming an angle of 12° on either side of the sectional plane II of FIG. 1a.

The bores of areas 1 to 3 decrease progressively from the opening 100 to the shoulder 300 so that tightening of the case in the cap is more effective. The bore of the area 4 is even more clearly conical.

FIG. 2 makes it possible to define at least three adjacent areas of the case for protecting the syringe body:

the cylindrical area 20 in which are situated the complementary means for fixing the case in the cap, the length of the area 20 is fixed arbitrarily at the total of the lengths of the areas 1,2,3 of the cap covering the case when the opening 21 of the case abuts against the shoulder 400 of the cap;

the cylindrical area 30, defines adjacent the blind hole of the case by a step 31 corresponding to the contraction supporting the needle of the syringe contained in the case so that the needle is not able to touch the blind base 51 of the case;

the polygonal area 40 corresponding to the part of the syringe, itself polygonal, supporting the needle, so that the syringe is not able to rotate inside the case;

the conical area 50, terminated by the blind base 51 which serves as a protective covering for the needle.

The complementary means for fixing the case in the cap are constituted by identical parts in relief, in the form of angle members 22, orientated in the same direction in order that the internal rightangles 23 are on a single circumference parallel to the rim 24 of the opening 21. The sides 25 of the angle members perpendicular to the axis of symmetry XX common to the case and to the cap, lie flush with the rim 24 of the opening 21. The angle 26 of these sides is slightly chamfered.

These angle members 22 are equidistant on the outer periphery of the area 20 of the case, the space which separates them one from the other is slightly greater than the width of the rectangles 200, which in the example described corresponds to an angular distance of 30° between opposite ends 27,28 of each side 25.

FIG. 2a shows a section of the case along a line BB which indicates the distribution of the angle members 22 on the periphery of the case, particularly the stagger of their angular position with respect to the angular position of the rectangles 200.

Starting from a plane of symmetry YY at right angles to the axis of symmetry XX, the face 20 of the rightangles 23 of each angle member 22 forms an angle of 9° with the plane YY and the parallel face 28 of the side 22 forms an angle of 36° with the plane YY, in order that between two parallel faces 28 of each side 25 of the angle member 22 flush with the opening 21, there is an angular distance of 90°.

Placing the cap on the case introduces the rectangles 200 between the angle members 22 until the rim 24 of the opening 21 abuts against the shoulder 300 of the cap. A rotation of the cap causes the rectangles 200 to slide in the angle 23 of the angle members where they hold the cap firmly on the case.

What is claimed is:

1. Case for protecting a syringe body constituted by a hollow tubular member which fits tightly on the outer face of the body, one end of this member being closed off by a solid wall, the length of the case being such that when the body is introduced into the latter, the tip for fixing the syringe on a gripping tool remains exposed and the needle which projects outside the body is protected in an air-tight manner, inside the case, without contact with the inner faces of the latter, the case being provided internally with an abutment which limits the penetration of the syringe body in the case so that the needle does not reach the closing wall, the open end of the case being closed by a removable blind cap having an inner diameter corresponding to the outer diameter of said end of the case so that this cap constitutes a virtually air-tight closure enclosing and protecting the syringe body in the case, characterised by the fact that its open end comprises, also distributed on the outer periphery of the case along equidistant generatrices parallel to the axis of symmetry of the case, parts in relief of identical thickness, in the form of angle members whereof one side namely the side which is oriented towards the opening of the case, is situated on a single circumference parallel to the rim of said opening, the apex of each internal rightangle being situated on another single circumference which is parallel to the former and by the fact that the cap comprises, also distributed on its inner periphery in contact with the case along equidistant generatrices, parallel to its axis of symmetry, parts in relief of identical thickness, in the form of rectangles whereof the same side, directed towards the opening in the cap, is situated on a single circumference parallel to the rim of the opening in the cap, the peripheral spacing between the rectangles corresponding to the peripheral spacing between the sides of the angle members parallel to the axis of symmetry common to the case and to the cap, so that positioning of the cap on the case introduces the rectangles between the angle members and that a rotation of the cap with respect to the case places these rectangles in the rightangles of the angle members all orientated in the same direction in order to ensure locking of the cap on the case.

2. Case for the protection of a syringe body according to claim 1, characterized by the fact that the blind cap comprises internally a circular shoulder parallel to the rim of its opening and by the fact that this shoulder is located at a distance from said rim such that locking of the cap on the case presses said shoulder in an air-tight mannere on the peripheral rim of the opening of the case.

3. Case for the protection of a syringe body according to claim 2, characterized by the fact that the cap is in one piece and comprises two parts separated by a step, one being open and cylindrical covering the case, the other being closed a polygonal allowing gripping and operation of said cap, in particular for locking.

4. Case for the protection of a syringe body according to claim 3, characterised by the fact that the cylindrical part of the cap comprises at least two separate bores separated by a shoulder formed by the area joining the bore which is largest and closest to the opening to the smallest bore which adjoins the step, the blind part following these two bores being polygonal, these three parts having a common axis of symmetry.

5. Case for the protection of a syringe body according to claim 4, characterised by the fact that the peripheral rim of the opening of the cap comprises a chamfer directed towards the inside of the bore of greatest diameter.

* * * * *